United States Patent [19]
Wittkampf

[11] Patent Number: 6,063,078
[45] Date of Patent: May 16, 2000

[54] METHOD AND APPARATUS FOR TISSUE ABLATION

[75] Inventor: Frederik H. M. Wittkampf, Bilthoven, Netherlands

[73] Assignee: Medtronic, Inc., Minneapolis, Minn.

[21] Appl. No.: 08/815,819

[22] Filed: Mar. 12, 1997

[51] Int. Cl.$^7$ ............................................ A61B 18/18
[52] U.S. Cl. ........................ 606/41; 606/49; 607/102
[58] Field of Search ........................... 606/41, 42, 49, 606/34; 607/100–102, 122

[56] References Cited

U.S. PATENT DOCUMENTS

| | | |
|---|---|---|
| 5,045,056 | 9/1991 | Behl . |
| 5,122,137 | 6/1992 | Lennox . |
| 5,423,808 | 6/1995 | Edwards et al. . |
| 5,429,131 | 7/1995 | Scheinman et al. . |
| 5,456,682 | 10/1995 | Edwards et al. . |
| 5,492,119 | 2/1996 | Abrams . |
| 5,500,012 | 3/1996 | Brucker et al. . |
| 5,562,721 | 10/1996 | Marchlinski et al. ............... 607/99 |
| 5,697,925 | 12/1997 | Taylor ............................ 606/34 |
| 5,702,386 | 12/1997 | Stern et al. ...................... 606/34 |
| 5,722,975 | 3/1998 | Edwards et al. .................. 606/34 |

OTHER PUBLICATIONS

Radiofrequency Ablation of Cardiac Arrhythmias—Scientific American Science and Medicine—May/Jun. 1994, (L.S. Klein and W. M. Miles).

Thermistor Guided Radiofrequency Ablation of Atrial Insertion Sites in Patients with Accessory Pathways—PACE, vol. 18, Nov. 1995, pp. 2001–2007, (C.M. Tracy et al.).

The Biophysics of Radiofrequency Catheter Ablation in the Heart: The importance of Temperature Monitoring—PACE, vol. 16, Mar., Part II 1993, pp. 586–591 (D.E. Haines).

*Primary Examiner*—Linda C. M. Dvorak
*Assistant Examiner*—Roy Gibson
*Attorney, Agent, or Firm*—Thomas F. Woods; Harold Patton; Michael J. Jaro

[57] ABSTRACT

The present invention is a system for ablating tissue within a body, the system having: an energy source providing a level of energy which is non damaging to the cellular structures of the body tissue, a catheter coupled to the energy source, the catheter having an electrode; and means for sensing the temperature of the electrode while also sensing the amount of energy which is non damaging to the cellular structures of the body tissue is delivered to the electrode, the sensing means coupled to the catheter and coupled to the energy source wherein the degree to which the electrode contacts the heart tissue (e.g. no contact, moderate contact, good contact or excellent contact) may be determined.

12 Claims, 11 Drawing Sheets

METHOD AND APPARATUS FOR TISSUE ABLATION

FIELD OF THE INVENTION

This invention relates generally to the field of devices for cardiac surgery, and more specifically to devices for R-F ablation of cardiac tissue.

BACKGROUND OF THE INVENTION

The present invention is directed toward treatment of tachyarrhythmias, which are excessively fast heart rhythms. In particular, the present invention is directed toward treatment of tachycardias.

Therapies have been developed for treating tachycardias by destroying cardiac tissue containing identified ectopic foci or aberrant conduction pathways. A variety of approaches have been taken, including application of electrical energy or other forms of energy to destroy the undesired cardiac tissue. As examples, ablation of cardiac tissue has been accomplished by means of radio frequency electrical current, microwave energy, heat, electrical pulses, cryothermy, and lasers. At present, ablation using R-F energy is perhaps the most widely practiced in the context of ablation procedures that can be carried out by means of a catheter, inserted into the closed heart.

Most R-F ablation catheters employ electrodes which are intended to contact the endocardium or, in some cases as in U.S. Pat. No. 5,083,565, are intended to penetrate the endocardium, and enter the myocardium. In general, R-F ablation catheters are effective to induce small lesions in heart tissue including the endocardium and inner layers of myocardium, in the immediate vicinity of the electrode.

R-F ablation causes tissue in contact with the electrode to heat through resistance of the tissue to the induced electrical current therethrough. Reliably sensing, however, when the electrode is in actual contact with the heart tissue so that the ablation procedure may begin is required. Many schemes for sensing electrode contact with the tissue have been proposed. For example, ablation systems of Biosense, Inc. detect wall contact through the stability of the sensed EKG. Such an approach is not completely satisfactory. In patients who have an infarction, for example, the tissue near the infarction often cannot provide an acceptable EKG signal. Ablating near the infarcted area, however, is often times the specific area in which ablation is needed to be performed. Still further, the stability of the EKG actually only indicates the stability of contact during the 50–100 ms in which the P or QRS complex is present. The electrode may still bounce against the moving heart wall and still provide a stable EKG signal. Other ablation systems, such as those sold by the CarioRythm division of Medtronic Inc., detect wall contact through impedance. This approach is also not completely satisfactory. Displacement or movement within the heart of the ablation catheter relative to the indifferent skin electrode alters the impedance detected, thus distorting the detection of wall contact. Moreover, such measurements may also vary from patient to patient. Finally, the variations in impedance due to wall contact are often too small to be a reliable indicator of actual wall contact. Thus there exists a need for and ablation system which permits the electrode tissue contact to be reliably indicated.

SUMMARY OF THE INVENTION

The present invention is a system for ablating tissue within a body, the system comprising: an energy source providing a level of energy which is non damaging to the cellular structures of the body tissue, a catheter coupled to the energy source, the catheter having an electrode; the system further having means for sensing the temperature of the electrode while also sensing the amount of energy which is non damaging to the cellular structures of the body tissue (i.e. non ablative) is delivered to the electrode wherein the degree to which the electrode contacts the heart tissue (e.g. no contact, moderate contact, good contact or excellent contact) may be determined. In the preferred embodiment the non-damaging energy delivered to the body is less than 5 Watts and the catheter has a temperature sensor positioned within the distal end.

DESCRIPTION OF THE PREFERRED EMBODIMENTS

Figure 1:
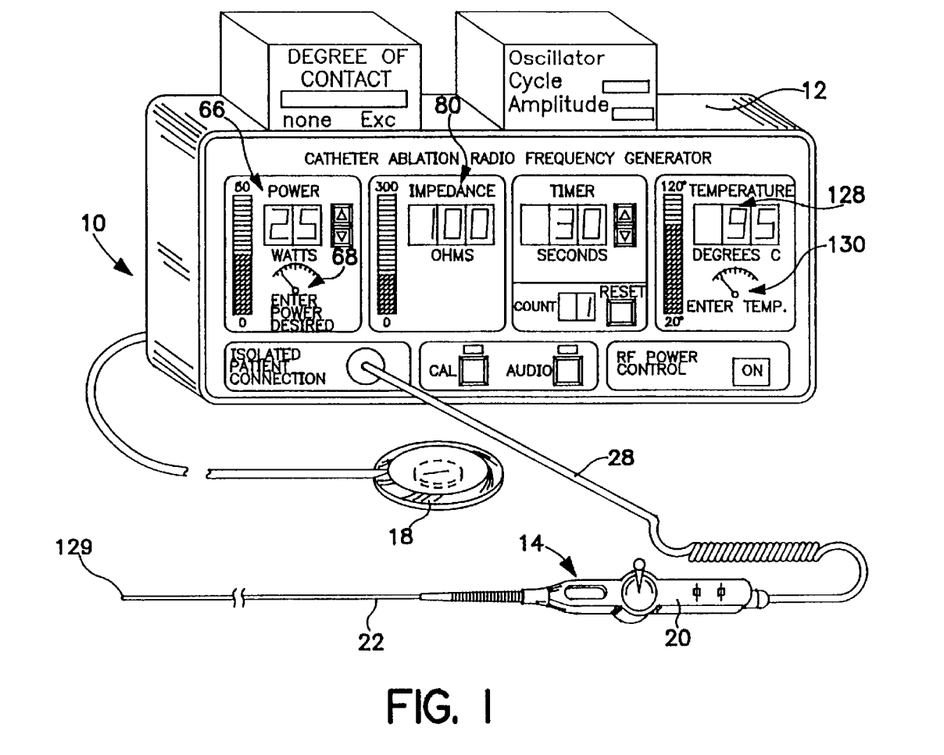
FIG. 1 shows a system for performing ablation on human tissue that embodies the features of the invention.

FIG. 1 shows a system 10 for performing ablation on human tissue that embodies the features of the invention. The system 10 includes a radio frequency generator 12 that delivers radio frequency energy ("RF energy"). Of course, other types of energy may also be used, such as microwave energy, heat, electrical pulses, cryothermy, and lasers. The specific type of energy delivered is not essential to the invention. The system 10 also includes a steerable catheter 14 carrying a radio frequency emitting tip electrode 129.

In the illustrated embodiment, the system 10 operates in a monopolar mode. In this arrangement, the system 10 includes a skin patch electrode that serves as an indifferent second electrode 18. In use, the indifferent electrode 18 attaches to the patient's back or other exterior skin area.

Alternatively, the system 10 can be operated in a bipolar mode. In this mode, the catheter 14 carries both electrodes.

In the illustrated embodiment, the ablation electrode 129 and indifferent electrodes 18 are made of platinum.

The system 10 can be used in many different environments. This specification describes the system 10 when used to provide cardiac ablation therapy.

When used for this purpose, a physician steers the catheter 14 through a main vein or artery (typically the femoral artery) into the interior region of the heart that is to be treated. The physician then further manipulates the catheter 14 to place the tip electrode 129 into contact with the tissue within the heart that is targeted for ablation. The user directs radio frequency energy from the generator 12 into the tip electrode 129 to form a lesion on the contacted tissue.

In the embodiment shown in FIG. 1, the catheter 14 includes a handle 20, a guide tube 22, and a tip portion, which carries the tip electrode 129. The handle 20 encloses a steering mechanism 26 for the catheter tip 24. A cable 28 extending from the rear of the handle 20 has plugs (not shown). The plugs connect the catheter 14 to the generator 12 for conveying radio frequency energy to the ablation electrode 16. The radio frequency heats the tissue to form the lesion.

One or more steering wires 132 (shown in FIG. 2) extend through the guide tube 22 to interconnect the steering mechanism 26 to the left and right sides of the tip 24. Rotating the steering mechanism 26 to the left pulls on the left steering wire, causing the tip having tip electrode 129 to bend to the left. Also, rotating the steering mechanism 26 to the right pulls on the right steering wire, causing the catheter tip to bend to the right. In this way, the physician steers the tip electrode 129 into contact with the tissue to be ablated.

The generator 12 includes a radio frequency power source 30 connected through a main isolation transformer 32 to first and second conducting lines. In the illustrated embodiment, the power source 30 delivers between 0–100 Watts of power at a frequency between 100 KHz–1 MHz. The first conducting line leads to tip electrode 129. The second conducting line leads to the indifferent patch electrode 18.

Figure 2:
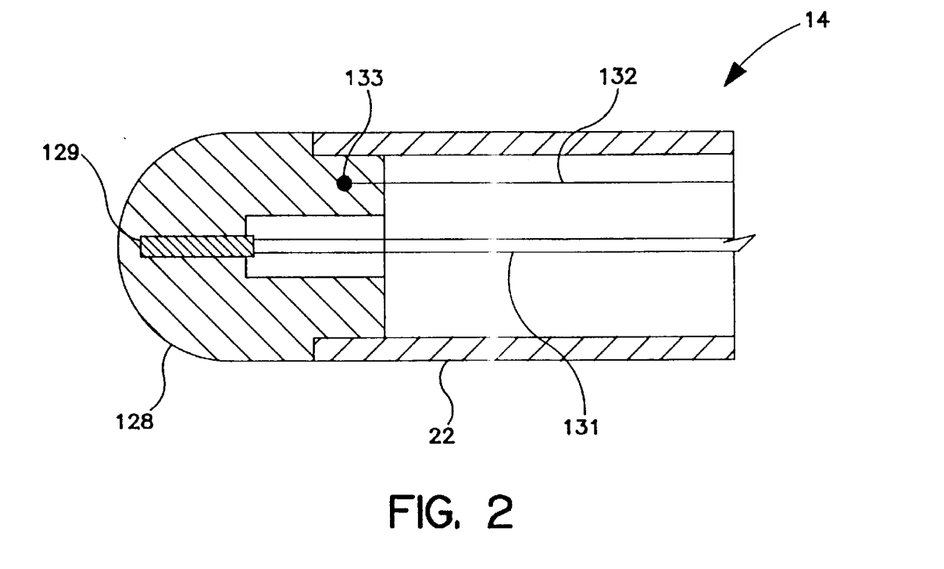
FIG. 2 is a sectional view of the distal end or tip of the catheter seen in FIG. 1.

FIG. 2 is a sectional view of the distal end or tip of the catheter 14 seen in FIG. 1. As seen catheter tip has electrode 128 mounted on catheter shaft 130. Electrode 128 is electrically coupled to power source (not shown in this FIG) through conductor 129. In the preferred embodiment electrode is a platinum alloy. Positioned within electrode is thermistor assembly 129. Although shown within electrode, thermistor may also be positioned on, adjacent to or separated from electrode. A pair of thermistor leads 131 couple to thermistor assembly and power source. Thermistor assembly is used to sense the temperature of the electrode, although other types of temperature sensors may also be used, such as a thermocouple for example. As discussed in more detail below, the degree to which the electrode contacts the heart tissue (e.g. no contact, moderate contact, good contact or excellent contact) may be determined by sensing the temperature of the electrode while also sensing the amount of energy which is non damaging to the cellular structures of the body tissue (or "non-ablative") is delivered to the electrode.

Figure 3:
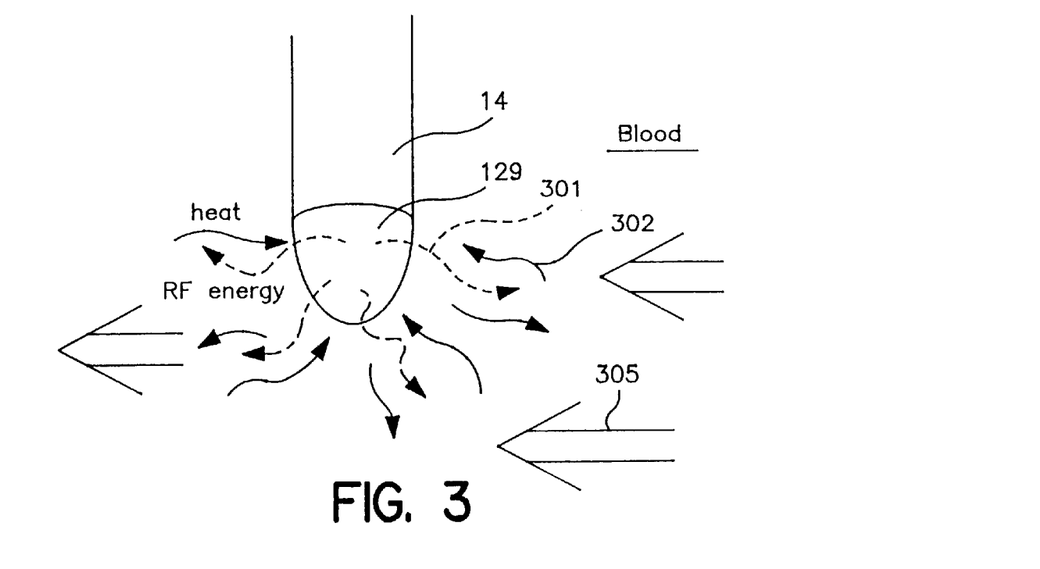
FIG. 3 illustrates a catheter tip having an electrode which is emitting energy into the blood stream and the resulting transmission of heat back into the catheter tip.

FIG. 3 illustrates a catheter tip having an electrode which is emitting energy into the blood stream and the transmission of heat back into the catheter tip. As discussed above, during RF ablation high frequency current is delivered to the tissue and fluids which contact the electrode. Because these tissues and fluids have some electrical resistivity, heat is generated within the tissues and fluids. This so-called resistive heating thereby causes energy in the form of heat to be transmitted back into the electrode. As seen, RF energy represented by dotted lines 301 is emitted from the electrode 129 of catheter 14. In return, heat, represented by solid lines 302, is created in the surrounding tissues and fluids, in this case the blood stream, and partially radiated back into the electrode. Thus the delivery of RF energy to the tissues or fluids of the body causes the electrode to also heat. In the present example, because the electrode is within the blood, however, less of the heat is radiated back into the electrode and more is carried away from the electrode by the blood flow 305 as compared to if the electrode was in contact with body tissue.

Figure 4:
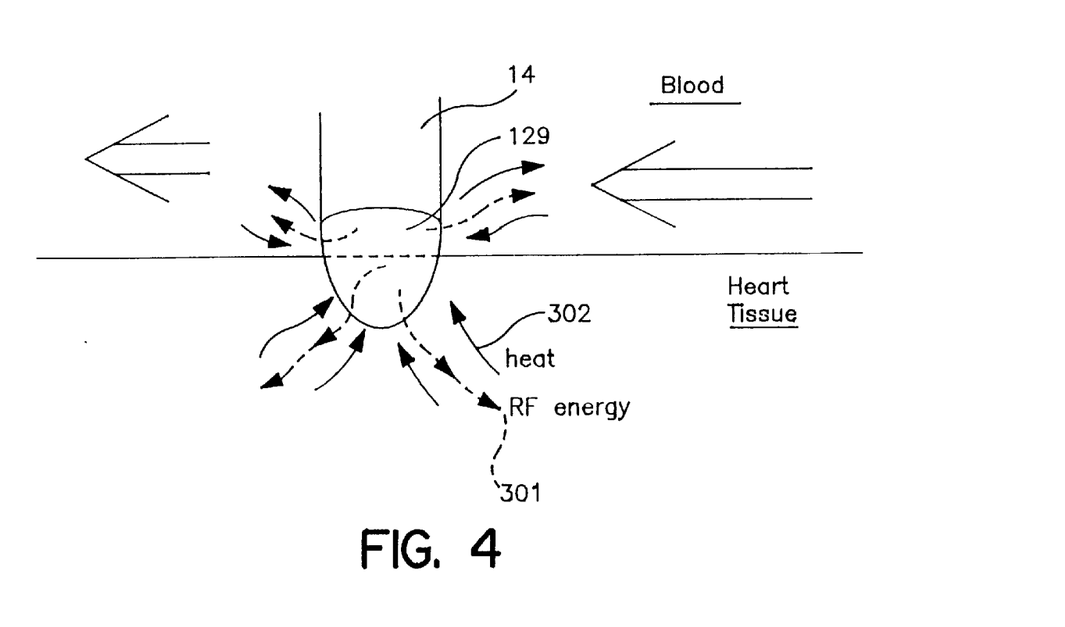
FIG. 4 illustrates a catheter tip having an electrode in contact with heart tissue and which is emitting energy into the tissue and the resulting transmission of heat back into the catheter tip.

FIG. 4 illustrates a catheter tip which is in contact with body tissue and which is emitting energy into tissue and the transmission of heat back into the catheter tip by the tissue. As seen, when the tip electrode is in contact with tissue, such as heart tissue, less surface area of the tip electrode is exposed to blood. Blood transmits less heat back into the tip electrode from the emitted RF energy than does tissue. Consequently, as illustrated in this FIG., when the tip electrode contacts the heart tissue more heat 302 is delivered from the heart tissue back to the electrode as compared to when the electrode is completely surrounded by blood. This characteristic provides for three related methods for detecting wall contact. First, assuming constant tip temperature is maintained by the delivery of energy to the electrode, then when the amount of energy required to maintain the constant tip temperature is decreased, the tip is contacting heart tissue. Likewise, assuming the amount of power is kept at a constant, then when the temperature of the tip increases at a constant power setting, the electrode is in contact with the heart tissue. Finally, because the heating efficiency of transmitting energy from the electrode and the resulting transmission of heat back into the electrode is greater the closer the electrode is to the wall, then by monitoring the amount of heating efficiency to increase the temperature of the tip electrode, the degree of wall contact may be detected. In each method it is an essential feature of the invention that the power supplied to the electrode and the resultant temperature of the electrode are non-damaging to the cellular structures of the body.

Figure 5:
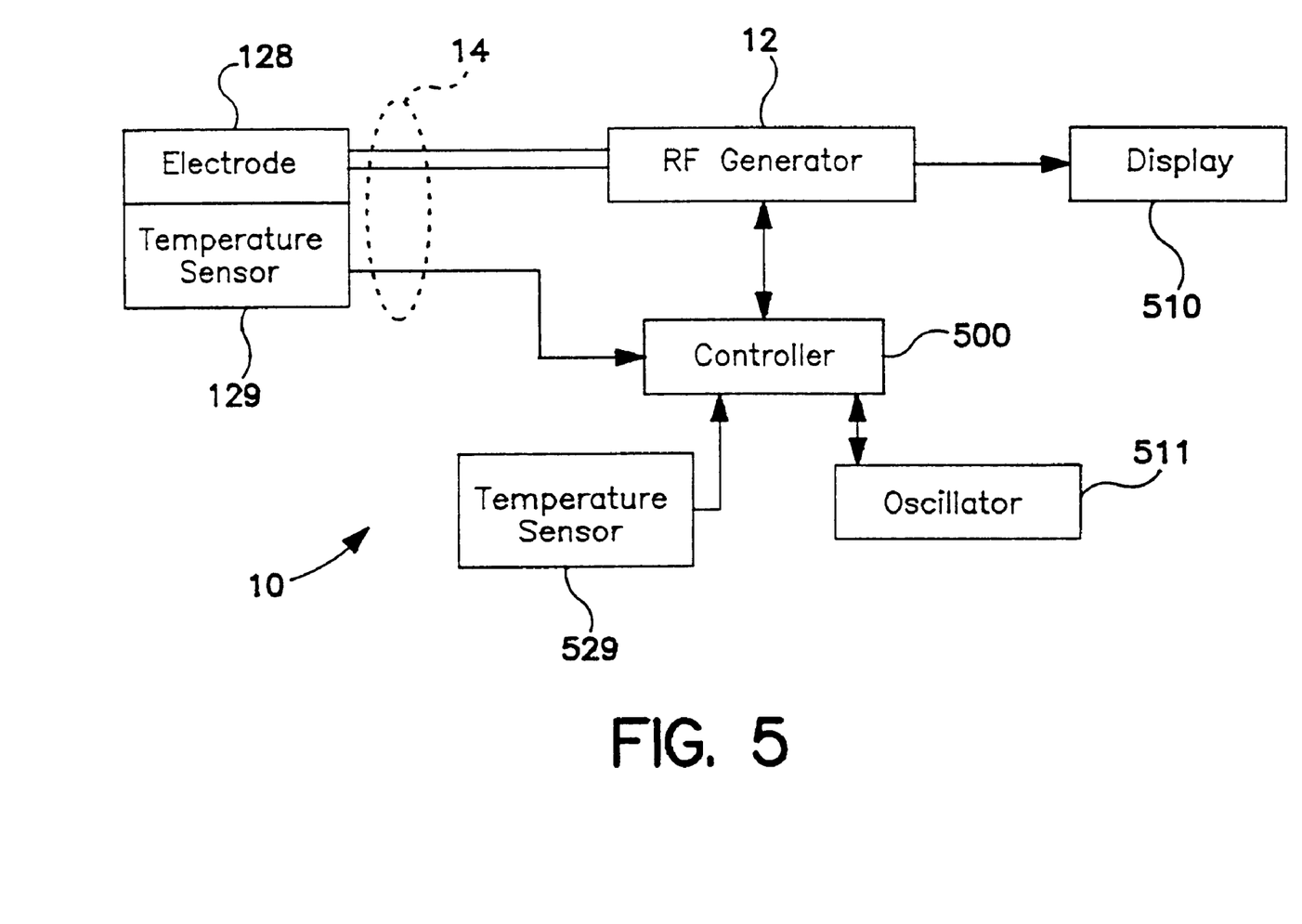
FIG. 5. illustrates a system for ablating tissue according to the present invention.

FIG. 5 illustrates a system for ablating tissue according to the present invention. As seen, the system 10 includes a RF generator 12 which is electrically coupled to electrode 128. Electrode is in catheter 14. Temperature sensor 129 is also located within the catheter and is preferably located within the electrode. Controller 500 is coupled to temperature sensor and to RF generator. Through controller, the amount of power delivered by RF generator to electrode may be controlled according to the sensor temperature of the electrode. As discussed above, this control may be aimed so that a constant power to the electrode is maintained, or a constant temperature of the tip electrode is maintained. Controller may also function to detect the heating efficiency of the power delivered to the electrode. Controller may be either a separate device or integral with the R-F generator.

In an alternative embodiment the system may further feature a second temperature sensor 529. In this embodiment the second temperature sensor would be located remote from the temperature sensor 129 but still in sensory contact with the body so that any variation in the body temperature of the patient during the ablation process may be corrected. Temperature sensor 529 may or may not be positioned along catheter 14. This additional temperature sensor is useful for those patients whose body temperature varies during the ablation catheterization procedure. For example, it is sometimes necessary to deliver a drug, such as isoproterenol, to mimic exercise and, in turn, induce arrhythmias. Such a drug, however, often causes the body temperature to rise 1 or 2 degree Celsius.

In a further alternative embodiment the system may also include display 510 to graphically output data indicating the degree to which the electrode contacts heart tissue (e.g. no contact, medium contact, etc.). Display may also provide data regarding the power delivered, electrode temperature or heating efficiency over time as further discussed below.

In a still further alternative embodiment, an oscillator 511 is either coupled to or provided within controller 500. Oscillator is used to cyclically vary the delivered energy to the electrode at a frequency between 0.01 Hz–1 Hz discussed below. Other alternative embodiments are also discussed below.

Figure 6:
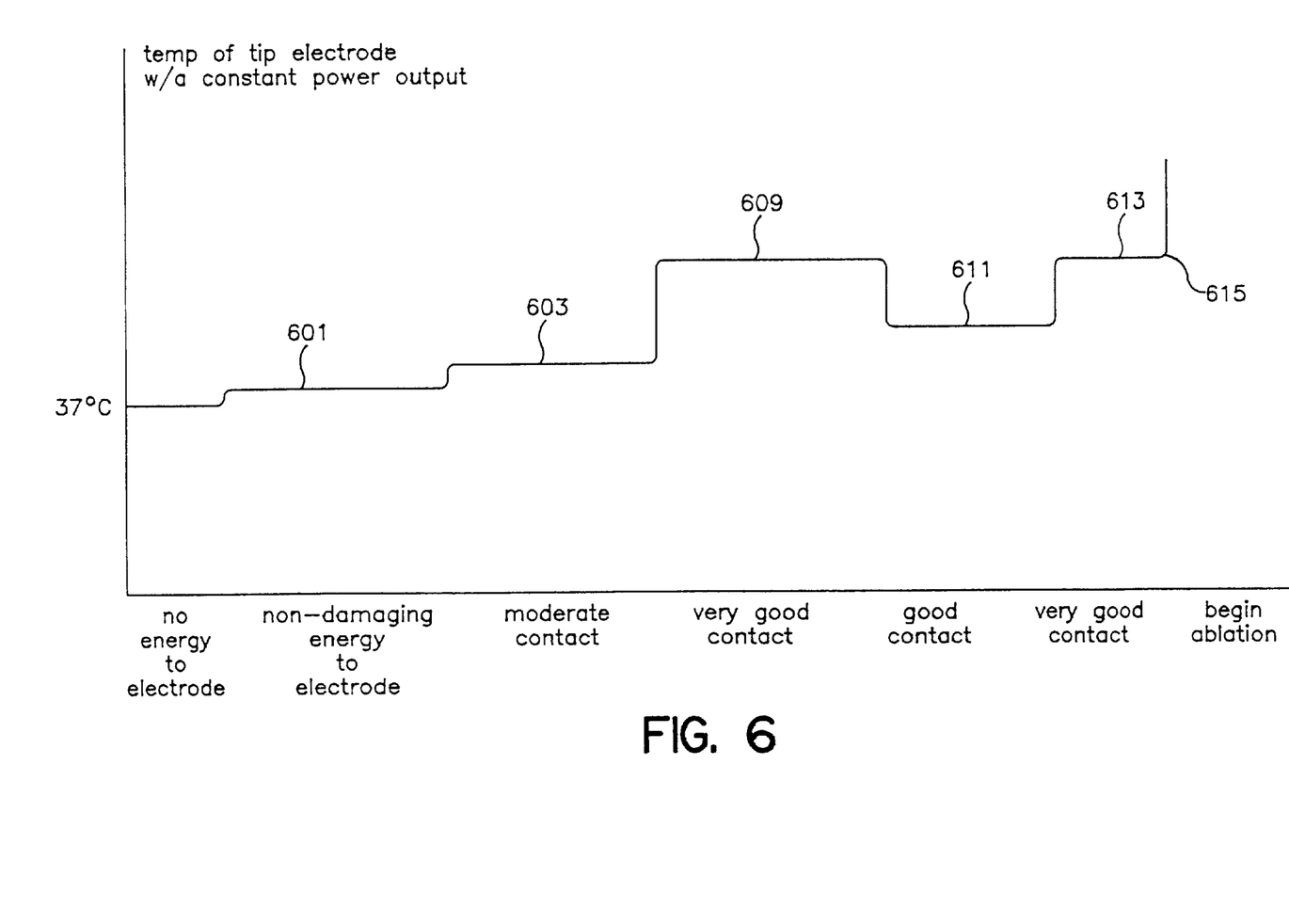
FIG. 6 illustrates the change in temperature of the tip electrode as it moves through the blood vessel and contacts heart tissue due to the delivery of a non-ablative amount of energy to the electrode.

FIG. 6 illustrates the change in temperature of the tip electrode as it moves through the blood and contacts heart tissue due to the delivery of a non-ablative amount of energy to tip electrode by generator. At 600 no energy is delivered to the electrode and the temperature of tip electrode is equal to body temperature, 37 degrees Celsius. As seen at 601, tip electrode has a temperature of approx. 38 degrees Celsius due to the delivery of a non-ablative amount of energy to tip electrode by generator. In the system illustrated the delivery of 1 Watt to an electrode which is 7 French wide and 5 mm long then a temperature rise of smaller than approx. 0.5 degrees Celsius in the tip electrode while it is in the blood. In the preferred embodiment this non-ablative amount of energy is no more than 5 Watts and is preferably less than 1 Watt. Of course the amount of energy delivered to the electrode and the temperature sensed in the electrode depend on the shape and size of the electrode. The essential aspect of the present invention is that an non-damaging amount of energy is delivered to the electrode and the temperature of the electrode is monitored. By monitoring the power delivered or the temperature created or the heating efficiency, then the degree of wall contact may be ascertained. At 603 the tip electrode has been moved into moderate contact with the heart tissue. As seen, due to the increased conduction of heat from tissue to tip electrode as compared to from blood to tip electrode, the temperature of the tip electrode rises. At 609 the tip electrode has been moved into excellent contact with the heart tissue and the temperature of the tip electrode has reached an equilibrium state at a higher temperature. Once tip electrode is removed from excellent contact with the heart tissue and is only in good contact with heart tissue, then the conduction of heat from tissue to tip electrode is relatively decreased and the temperature correspondingly decreases, as seen at 611. At 613 the tip has moved to very good contact with the heart tissue and the temperature of tip has again increased. As illustrated at point 615 an ablative amount of energy is delivered to tip electrode by generator to thereby ablate tissue.

Figure 7:
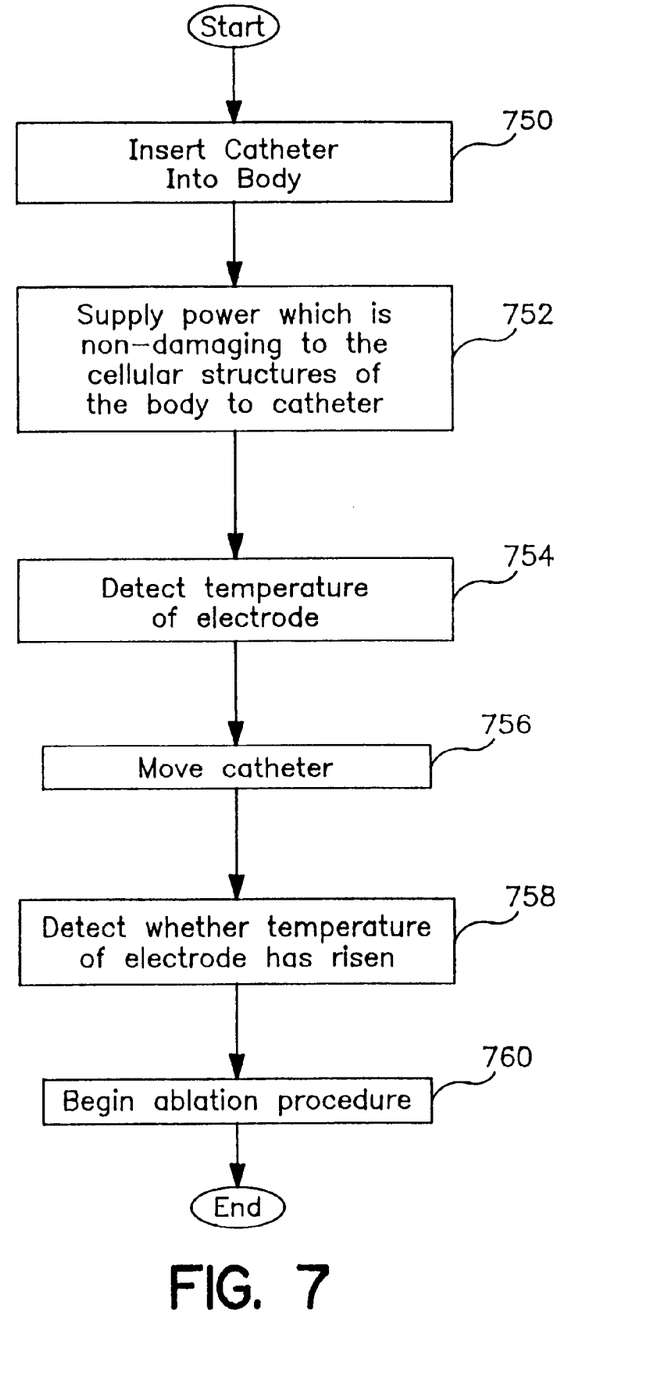
FIG. 7 depicts a method of determining heart wall contact of an ablation catheter by delivering an amount of power which is non-damaging to the cellular structures of the body.

FIG. 7 depicts a method of determining heart wall contact of an ablation catheter and ablating heart tissue using the present invention. As seen at 750 a catheter is inserted into the body and preferably into a blood vessel. Catheter preferably has a tip electrode having a temperature sensor, the electrode and sensor are coupled to a R-F generator having a controller as discussed above. At 752 power which is non-damaging to the cellular structures of the body is supplied to the catheter electrode. At 754 the temperature of the electrode is then sensed. As discussed above the supply of energy to the electrode will cause the electrode to increase in temperature by radiative heating, although the amount of heating will vary depending upon where the electrode is located, i.e. within the blood vessel or against the heart wall. At 756 the catheter is moved. At 758 the temperature of the electrode is again detected to determine whether it has risen. Assuming a constant amount of power is supplied to the electrode, then the rise in temperature of the electrode will indicate the degree of proximity of the electrode to the heart wall. Steps 756 and 758 are iterative, i.e., they are repeated until a desired result is obtained. Once the catheter is properly located then the ablation procedure may be begun, as depicted at step 760. Of course, the ablation process as depicted includes more than simply increasing the power supplied to the electrode but is also meant to include properly locating the electrode in the specific area of the heart tissue in which the ablative procedure is to be performed.

Figure 8:
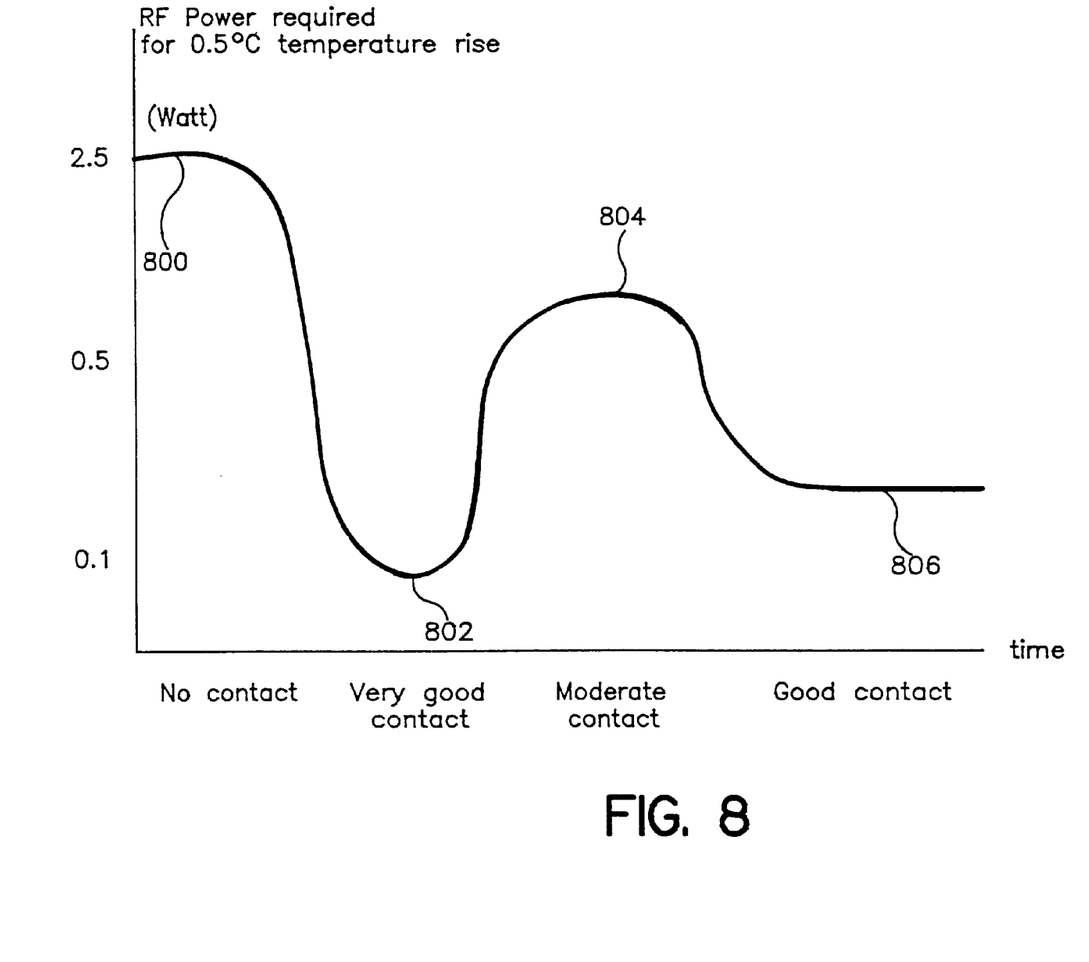
FIG. 8 illustrates the change in R-F power required for a 0.5° C. temperature rise in the electrode to be maintained as the electrode is moved towards and away from contact with heart tissue.

FIG. 8 illustrates the change in RF power required for a 0.5° C. temperature rise in the electrode to be maintained over time. As seen, at 800 tip electrode requires 2.5 Watts to maintain a 0.5° C. temperature rise. This would indicate there is no contact of the tip electrode with the heart wall. At 802 the RF power required has decreased to 0.1 watt. This would indicate that the tip electrode now is in very good contact with the heart wall. At 804 the catheter has been further moved and now requires over 0.5 watts to maintain a 0.5° C. rise in electrode temperature. This would indicate only moderate contact exists between the tip electrode and the heart wall. Finally, at 806 the RF power requires for a 0.5° C. rise in temperature has fallen to approximately 0.3 watts. As seen, this indicates there is now good contact between the heart wall and the tip electrode. Of course, other predetermined increases in temperature other than 0.5° C. may be selected, such as 1° C. Any temperature increase which is non ablative may be used.

Figure 9:
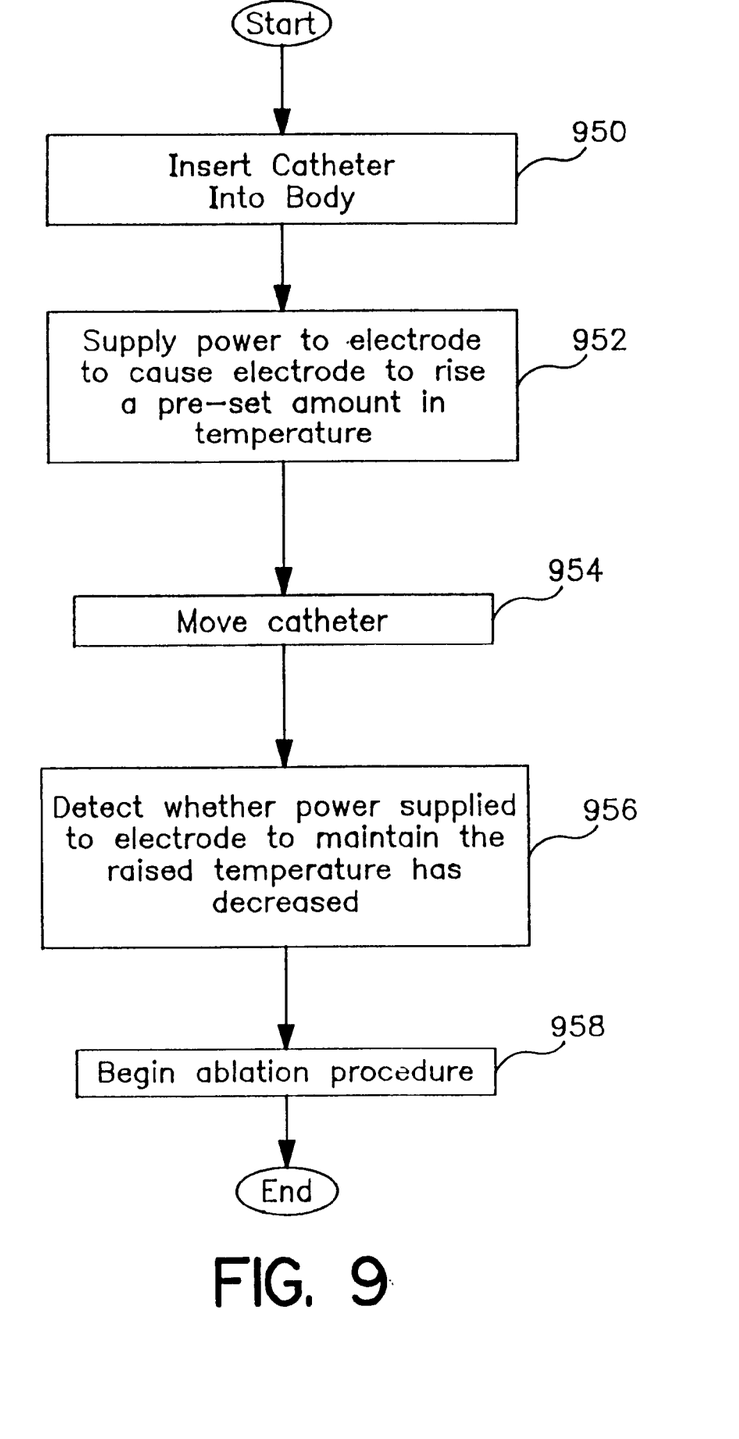
FIG. 9 illustrates a method of determining heart wall contact of an ablation catheter by supplying a non-damaging amount of power to the electrode to cause a pre-set rise in the temperature of the electrode.

FIG. 9 depicts a method of determining heart wall contact of an ablation catheter by maintaining a constant temperature rise at the catheter electrode and monitoring the required power to maintain that rise. The method begins at step 950 by inserting a catheter having an electrode and temperature sensor within the body, preferably within a blood vessel leading to the heart. At 952 an amount of power is supplied to the electrode to cause the temperture of the electrode to rise a preset amount. This preset rise in electrode temperature is no more than a temperature which is non-damaging to the cellular structures of the body. At 954 the catheter is moved. At 956 the amount of power required to maintain the electrode at the preset increase in temperature is detected. If the amount of power required is decreased, then the electrode is in better contact with tissue. Steps 954 and 956 are iterative and should be repeated until an acceptably low power level is required by the electrode. At 958 ablation procedure is begun. As discussed above in regards to FIG. 7 ablation procedure is used in the broadest possible manner and is simply intended to mean that the electrode is now in contact with tissue and a determination must be made whether the specific tissue the electrode is in contact with should be ablated.

Figure 10:
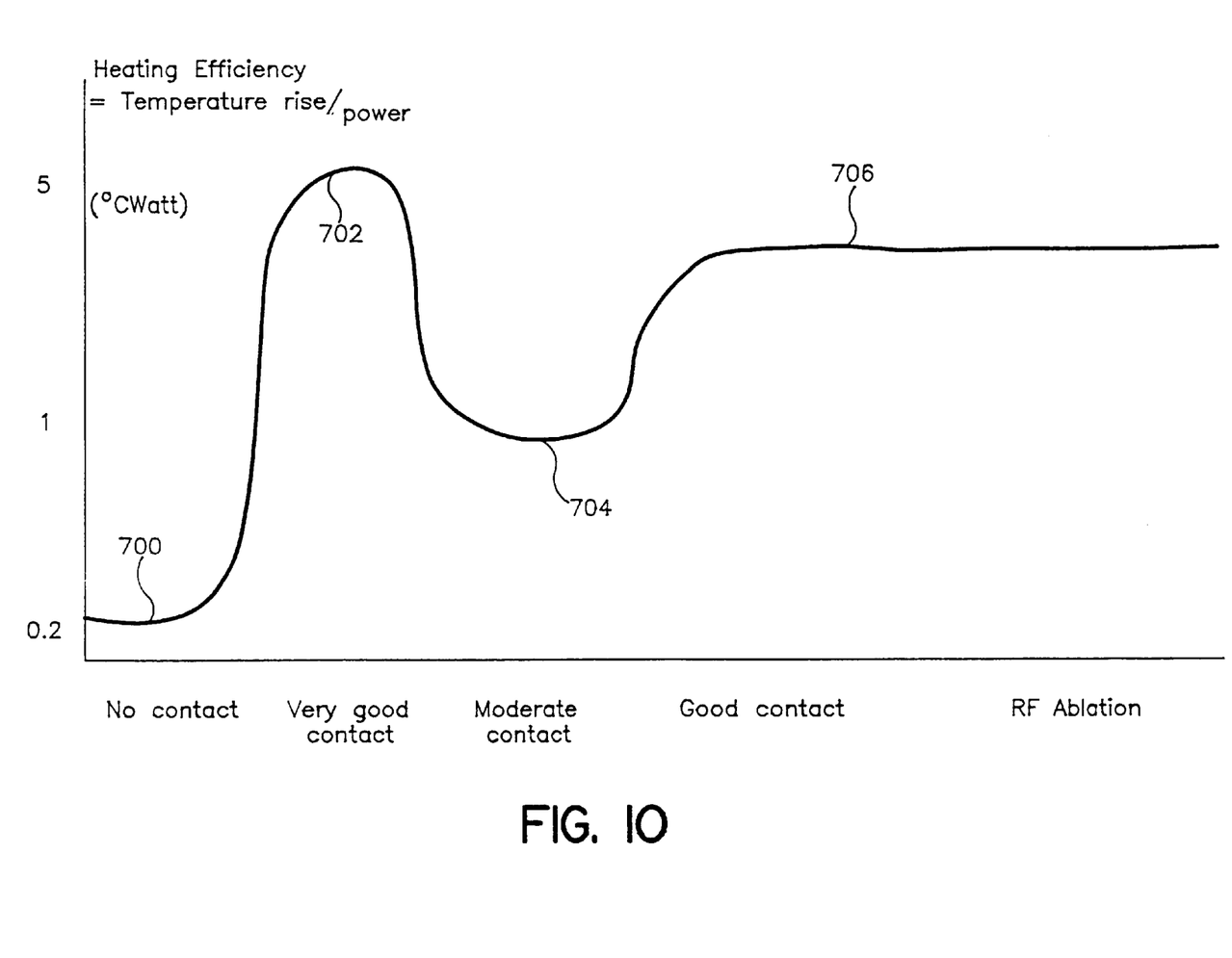
FIG. 10 illustrates the change in heating efficiency of the electrode as it moves into contact with the heart tissue.

FIG. 10 illustrates the change in heating efficiency of the tip electrode as it moves from the blood vessel, contacts the heart tissue and the ablation process is begun. Heating efficiency is the rise in temperature experienced at the tip electrode as compared to the power delivered. As seen at 700 the heating efficiency is very low, roughly 0.25° C./watt. At 702 the efficiency is increased to almost over 5° C./watt. This indicates there is very good contact between the tip electrode and the heart wall. At 704 the catheter has been moved and the heating efficiency is decreased now to 1° C./watt. This would indicate there is only moderate contact between the tip electrode and the heart wall. At 706 the catheter has been further moved and the heating efficiency is increased to roughly 4° C./watt. This would indicate there is good contact between the electrode and the heart wall. Once good contact is made the RF ablation process may be begin as illustrated. As illustrated the RF ablation process has a constant heating efficiency assuming the contact of the electrode to the tissue is constant. Thus using this method the degree of wall contact of the electrode can be monitored during the R-F ablation.

Figure 11:
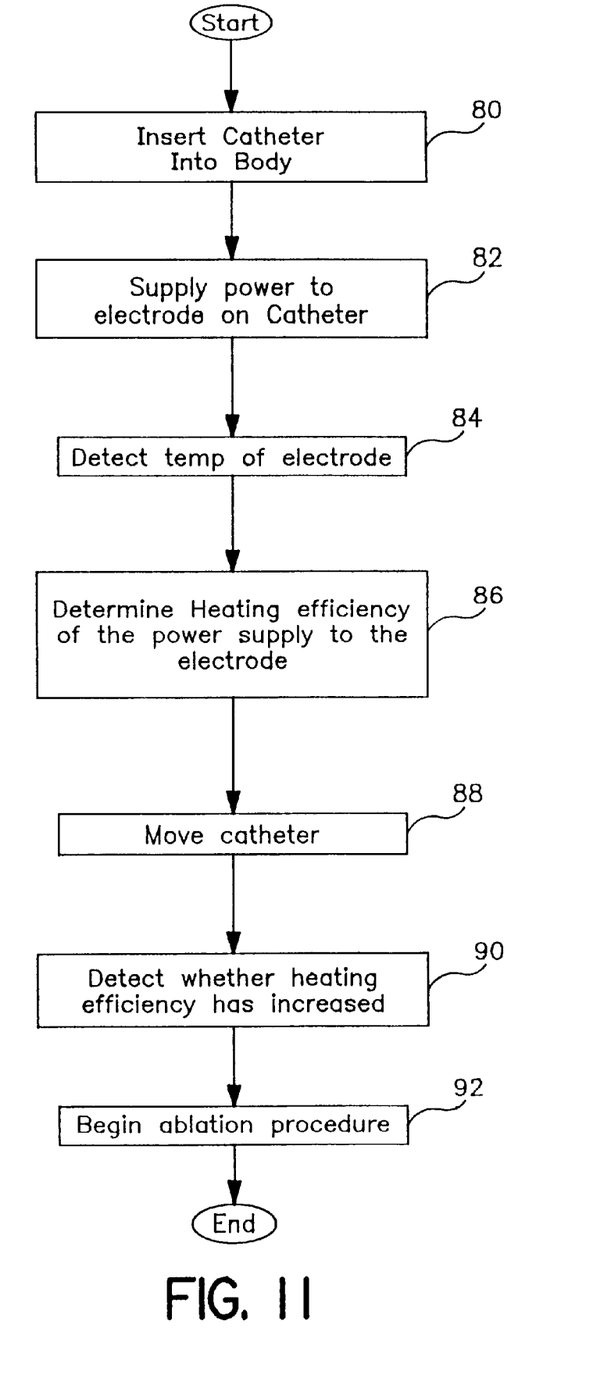
FIG. 11 depicts a method of determining heart wall contact by monitoring the heating efficiency of power supplied to the electrode.

FIG. 11 depicts a method of determining heart wall contact by measuring the change in heating efficiency of the tip electrode. At 80 a catheter is inserted into the body, preferably a blood vessel leading to the heart. At 82 power is supplied to the electrode. The amount of power supplied is preferably within a range which would not cause damage to the cellular structures of the body. At 84 the temperature of the electrode is detected. At 86 the heating efficiency of the power supplied to the electrode is determined. At 88 the catheter is moved through the blood vessel, preferably towards contact with the heart wall tissue. At 90 whether the heating efficiency of the power supplied to the electrode has increased is detected. Steps 88 and 90 are iterative and should be repeated until the desired heating efficiency is attained. Finally, at 92 the ablation procedure may be begun.

Figure 12:
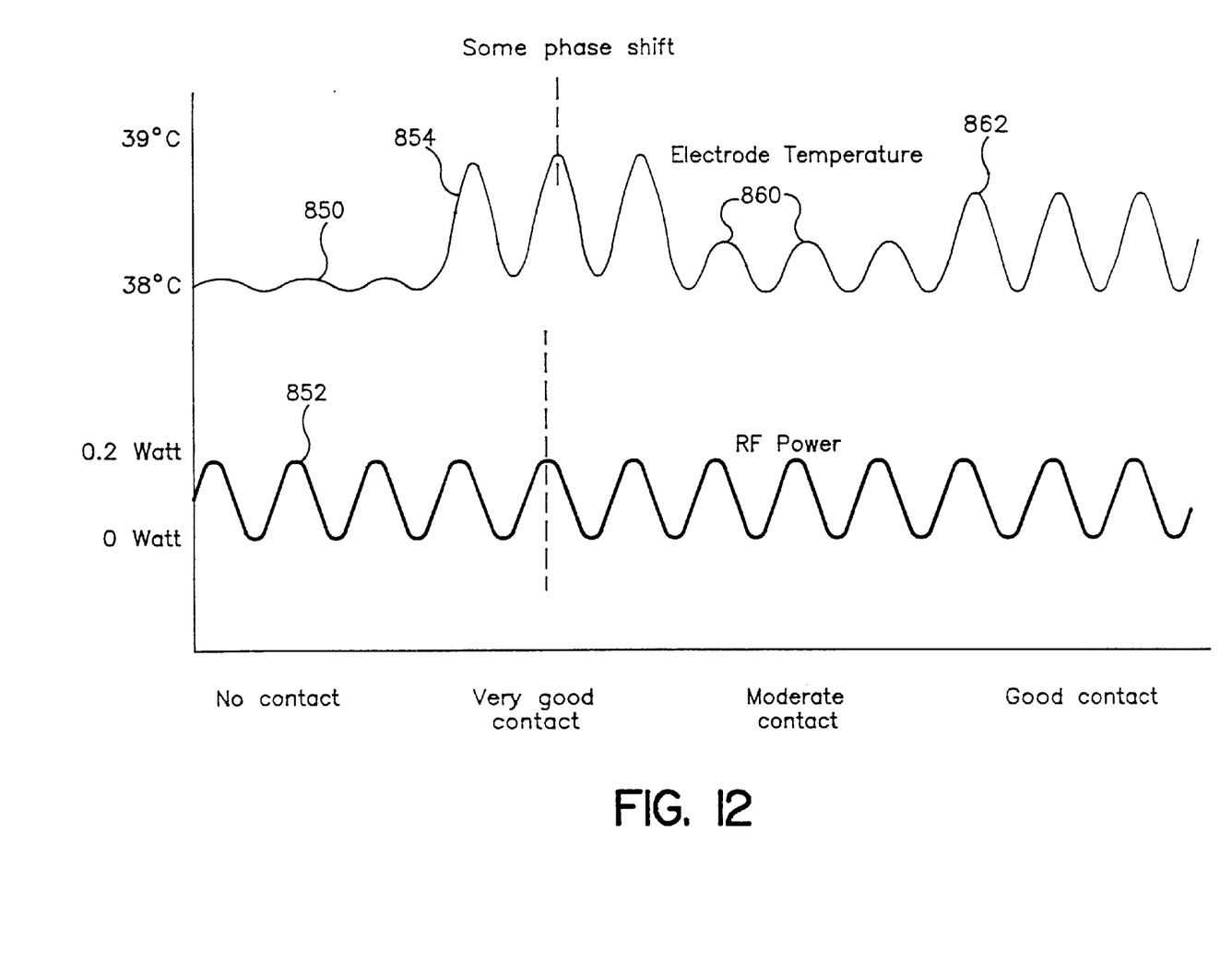
FIG. 12 illustrates the operation of a further embodiment of the present invention.

FIG. 12 illustrates the operation of further embodiment of the present invention. As discussed above, the temperature of the patient's body may vary during the ablation process. This may provide problems with indicating the quality of wall contact of the tip electrode. In this alternative embodiment this problem is overcome through the use of a cyclic delivery of non-damaging amount of RF energy to the tip electrode and the corresponding sensing of the temperature in the tip electrode. As seen at 852 a cycle of RF energy between 0–0.2 watts is delivered to the electrode. At this time the electrode temperature undergoes a slight change in temperature as illustrated at 850. Once wall contact is achieved, then the sensed electrode temperature will also undergo a cyclic variation as illustrated at 854. Moreover, there will be a phase shift between the sensed temperature of the electrode and the delivery of the RF energy while any contact is maintained. This phase shift will result from the lag in time of the power being delivered to the tissue, the tissue heating, and the radiation of the tissue heat back into the tip electrode and the sensing of this heat by the temperature sensor. If the electrode is further moved and only moderate contact is made between the tip electrode and the heart tissue, then the amplitude of the temperature variation of the electrode will decrease as seen at 860. Once good or better contact is satisfactorily achieved, then the amplitude of the temperature variation at the tip electrode will increase again as illustrated at 862.

Figure 13:
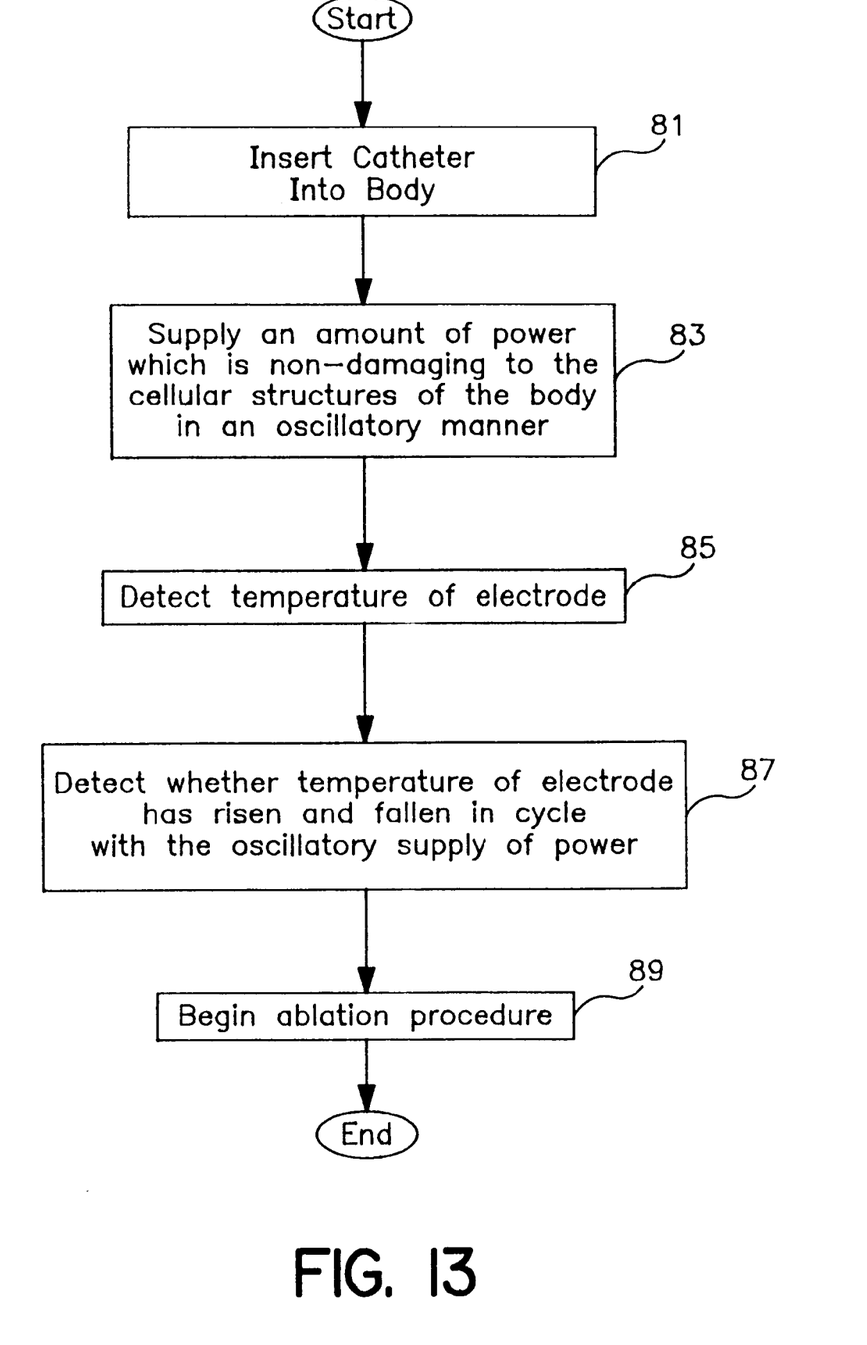
FIG. 13 depicts a method of determining a heart wall contact by supplying a cyclical amount of energy to the electrode and detecting whether there is a corresponding cyclic variation of temperature in the electrode.

FIG. 13 depicts a method of determining heart wall contact through the use of a cyclic delivery of a non-damaging amount of energy to the electrode and the corresponding sensing of the temperature variation in the tip electrode. At 81 the catheter having a tip electrode is inserted into the body, preferably a blood vessel lead to the heart. At 83 an amount of power which is non-damaging to the cellular structures of the body is supplied to the electrode in a cyclic or oscillatory manner. At 85 the temperature of the tip electrode is detected. At 87 whether the temperature of the tip electrode has risen and fallen in a cycle which corresponds to the oscillatory supply of power is detected. Steps 85 and 87 are iterative and should be repeated until a temperature variation in the electrode which is in a cycle corresponding to the power supplied and which also shows a sufficient amplitude of temperature variance is achieved. At 89 the ablation process is begun.

Although the invention has been described in detail with particular reference to a preferred embodiment and alternate embodiments thereof, it will be understood variations and modifications can be effected within the scope of the following claims. Such modifications may include substituting elements or components which perform substantially the same function in substantially the same way to achieve substantially the same result for those described herein.

What is claimed is:

1. A system for ablating cardiac tissue located within a human body, the system being configured to access the cardiac tissue via blood vessels in the body, comprising:

a power source for providing energy at a controllable rate to the cardiac tissue, the power source being capable of providing energy at a rate which is non damaging to cellular structures of the cardiac tissue, a catheter operatively coupled to the power source, the catheter having an electrode disposed at a distal end thereof, the electrode being configured to receive energy from the power source and distribute a portion thereof to the cardiac tissue; and means for sensing the rate at which energy is provided by the power source to the electrode, the means for sensing producing a second energy rate providing information;

means for sensing a temperature of the electrode attached to the catheter, the temperature sensing means providing first temperature information;

means for determining and controlling the rate at which energy is provided to the electrode by the energy source, the energy rate determining and controlling means receiving the first temperature information and the second energy rate providing information, the energy rate determining and controlling means determining on the basis of the first and second information a degree of contact of the electrode with the cardiac tissue and adjusting the rate at which the energy is provided to the electrode by the power source in accordance with the degree of contact determined thereby.

2. The system according to claim 1, wherein the power source further comprises means for providing a level of energy to the catheter that is non-damaging to the cellular structures of the cardiac tissue.

3. The system according to claim 1, wherein the temperature sensing means further comprises a thermistor positioned adjacent the electrode.

4. The system according to claim 1, wherein the energy rate determining and controlling means further comprises means for adjusting the level of energy provided to the electrode when the temperature sensed by the temperature sensing means increases by no more than 5 degrees Celsius.

5. The system according to claim 1, wherein the energy rate determining and controlling means further comprises means for adjusting the level of energy provided to the electrode when the temperature sensed by the temperature sensing means increases by no more than one half degrees Celsius.

6. The system according to claim 1, wherein the energy rate determining and controlling means further comprises means for adjusting the level of energy provided to the electrode when the level is substantially constant and non-damaging to the cellular structures of the cardiac tissue.

7. The system according to claim 1, wherein the energy rate determining and controlling means further comprises means for adjusting the level of energy provided to the electrode such that the level is non-damaging to the cellular structures of the cardiac tissue in response to receiving first temperature information exceeding a predetermined threshold.

8. The system according to claim 1, wherein the power source is an RF generator.

9. The system according to claim 8 wherein the RF generator operates at frequencies between 100 KHz and 1 MHz and provides an output of 0–100 Watts.

10. The system according to claim 1, wherein the energy rate determining and controlling means further comprises means for adjusting the level of energy provided to the electrode such that the level is decreased in response to the first temperature information and the second energy rate information indicating a decreased degree of contact of the electrode with the cardiac tissue.

11. The system according to claim 1, wherein the energy rate determining and controlling means further comprises means for adjusting the level of energy provided to the electrode such that the level is increased in response to the first temperature information and the second energy rate providing information indicating an increased degree of contact of the electrode with the cardiac tissue.

12. The system according to claim 1, wherein the energy rate determining and controlling means further comprises means for adjusting the level of energy provided to the electrode such that the level is held substantially constant in response to the first temperature information and the second energy rate providing information indicating a substantially constant degree of contact of the electrode with the cardiac tissue.

* * * * *